(12) United States Patent
Saghiri et al.

(10) Patent No.: US 8,668,770 B2
(45) Date of Patent: Mar. 11, 2014

(54) DENTAL CEMENT COMPOSITION

(76) Inventors: Mohammad Ali Saghiri, Tehran (IR); Mehrdad Lotfi, Tabriz (IR); Houtan Aghili, New York, NY (US)

( * ) Notice: Subject to any disclaimer, the term of this patent is extended or adjusted under 35 U.S.C. 154(b) by 245 days.

(21) Appl. No.: 13/211,880

(22) Filed: Aug. 17, 2011

(65) Prior Publication Data

US 2012/0012030 A1  Jan. 19, 2012

Related U.S. Application Data

(60) Provisional application No. 61/375,261, filed on Aug. 20, 2010.

(51) Int. Cl.
*A61K 6/06* (2006.01)

(52) U.S. Cl.
USPC ............. 106/35; 106/650; 106/813; 106/816; 977/919; 977/776

(58) Field of Classification Search
USPC ............ 106/35, 650, 813, 816; 977/919, 776
See application file for complete search history.

(56) References Cited

U.S. PATENT DOCUMENTS

| | | | |
|---|---|---|---|
| 7,942,963 B2 * | 5/2011 | Zimmermann | 106/690 |
| 8,475,811 B2 * | 7/2013 | Yang et al. | 424/400 |

* cited by examiner

*Primary Examiner* — Carol M Koslow
(74) *Attorney, Agent, or Firm* — Barry Choobin; Patent 360 LLC (57) ABSTRACT

Disclosed is a dental cement composition made up of ingredients comprising the nanoparticles of dicalcium and tricalcium silicate, bismuth oxide, gypsum, zeolite and strontium carbonate. The dental cement can also be used as bone cement, pulpotomy agent, pulp capping material, dental implant material, perforation repair material, and root-end filling material.

11 Claims, 6 Drawing Sheets

DENTAL CEMENT COMPOSITION

CROSS-REFERENCE TO RELATED APPLICATIONS

This application claims the benefit of U.S. provisional patent application Ser. No. 61/375,261 filed Aug. 20, 2010, which is incorporated herein by reference in their entireties.

FIELD OF THE INVENTION

The present invention is related to Endodontics, and more particularly to a dental cement composed of nanoparticle-elements or ingredients.

BACKGROUND OF THE INVENTION

Endodontics is a field of dentistry which deals with tooth pulp and the tissues surrounding the root of a tooth. Root canal treatment, endodontic retreatment and surgery, treating cracked tooth, and treating dental trauma are some of the endodontic procedures known in the art, of which, root canal treatment is one of the common procedures. Root canal treatments generally involve access to a tooth's root canal, removal of the tooth's pulp that includes the abscessed and dead tissues, disinfecting the root canal, enlarging the root canal, and removing irregularities or rough surfaces within the root canal. Following the root canal treatment, it is necessary to fill and to seal the evacuated root canal in order to prevent further ingress of microorganisms, which lead to recontamination thereof. Thus the pulp tissue and excised portions of the root should be replaced with dental cement or dental filling materials which are biocompatible to living tissues, bio-inert, and so on.

The most common dental filling material that used is Gutta-Percha, which is a natural resin and a thermoplastic rubber. However, the non-adhesive character of Gutta-Percha and the irregularities on the internal surface of the root canal makes it difficult to seal off the root canal completely. In order to overcome this limitation, sealants are used along with Gutta-Percha. An ideal root canal sealant should be biocompatible, anti inflammatory, antibacterial, bio-inert, non-toxic, radiopaque, and exhibit little to no shrinkage or, preferably, even expand slightly for better sealing. An ideal sealant should also have high wetting and low viscosity to seal the space between the filling material and the root canal walls.

Numerous sealants have been known in the art, for example, epoxy, calcium hydroxide, and zinc oxide eugenol-based sealers. During the root canal filling process, such materials are first applied to the Gutta-Percha, which is then inserted into the root canal. Alternatively, they may be inserted using a file or reamer applicator, so that the spaces between the Gutta-Percha points and the root canal walls can be sealed. However, controlling the exact amount of the sealant and/or filling material within the root canal to avoid over-extension or overfilling has long been a challenge for endodontists. For example, in case of overflow of root canal sealant from the apical foramen into the periradicular tissue during a root canal filling process, the excess material should be desirably tolerated by the surrounding tissue.

One of the drawbacks of conventional sealants is that they tend to be hydrophobic, making them incompatible with moist tissues within the root canal. Thus the hydrophilic nature of the root canal environment inhibits adequate penetration, complete wetting, and efficient adhesion of the hydrophobic sealant to the root canal walls. As a result, a poor seal is made between the Gutta-Percha and the root canal walls leading to re-entrance of microorganisms into the canal. In addition, overfilled Gutta-Percha and/or conventional sealant materials irritate the periapical soft tissues and do not stimulate healing and hard tissue formation. Moreover and most importantly, Gutta-Percha and conventional sealants degrade during long-term exposure to fluids present in the mouth.

Gutta-Percha and conventional sealants can also be used for root-end fillings, where the function of root-end filling materials is to interrupt all paths between the root canal system and its external surface. The root-end filling material should be antibacterial, nontoxic, noncorrosive, bio-inert, biocompatible, dimensionally stable, easy to handle, radiopaque, cost-effective, adaptable to the dentinal walls, and able to induce regeneration of bone and periodontal attachment. Root-end filling materials typically include Gutta-Percha (as mentioned before), an amalgam, reinforced zinc oxide eugenol cement, such as intermediate restorative material, glass ionomer cement, and/or mineral trioxide aggregate. However, typical root-end filling materials stain soft and hard tissues, leak from corrosion, are dimensionally unstable, are sensitive to moisture, and are expensive. To perform root perforation, the filling material should be able to fill the perforation site effectively and seal the avenue of communication between the oral cavity and the underlying periodontium.

White Mineral Trioxide Aggregate (WMTA) is another one of the commonly used dental cements, which is also used as a root-end filling material. While WMTA has many advantages including biocompatibility, good sealing ability, and antibacterial properties, it suffers from low pH resistance, which affects the microhardness, and long setting time. More particularly, the initial and final setting times of WMTA is about 40 minutes and more than 3 hours respectively, which is not desirable especially when used as a root-end filling material.

Pulp capping is another endodontic procedure, which is aimed at preserving the vitality of the pulp. The materials used for pulp capping must also be biocompatible, bioactive, nontoxic, and should not cause irritation to the pulp. An ideal material should also allow for the regeneration of surrounding tissue and dentine. Calcium hydroxide is a commonly used pulp capping material. However, calcium hydroxide has a very limited working time and is degradable by long-term exposure to tissue fluids that are commonly present in the mouth.

Therefore, in the light of the above discussion, there remains a need for a multi-purpose dental composition for use in root canal treatments, root-end filling procedures, and pulp capping, which nullifies the drawbacks of aforementioned dental materials used for the same.

SUMMARY OF THE INVENTION

It is an objective of the present invention to provide a dental cement composition which is bio-active and bio-compatible with dental tissues.

It is another objective of the present invention to provide a dental cement composition that stimulates quicker healing of the damaged dental tissues.

It is still another objective of the present invention to provide a dental cement composition that exhibits reasonably little shrinkage.

It is still another objective of the present invention to provide a dental cement composition that has low porosity.

It is yet another objective of the present invention to provide a dental cement composition that sets quicker in an aqueous environment.

It is still yet another objective of the present invention to provide a dental cement composition that exhibits antimicrobial properties.

It is still yet another objective of the present invention to provide a dental cement composition that demonstrates osteopromotive properties including Osteoconductivity, Osteoinductivity and Osteogenesis.

These and other objects and advantages of the embodiments herein will become readily apparent from the following detailed description taken in conjunction with the accompanying drawings.

DETAILED DESCRIPTION OF THE INVENTION

The present invention is a chemical composition of dental cement, which can also be used for other endodontic procedures including root-end filling, pulp capping, and so on. The dental cement composition is made up of ingredients comprising nanoparticles of Di-calcium Silicate ($Ca_2SiO_4$), Tri-calcium Silicate ($Ca_3SiO_5$), Bismuth Oxide ($Bi_2O_3$, Gypsum, Strontium Carbonate ($SrSO_4$), Zeolite, Calcium Sulfate ($CaSo_4$), Di-sodium Hydrogen Phosphate ($Na_2HPO_4$), Tri-calcium Aluminate ($Ca_3Al_2O_6$). A detailed breakup of the composition is tabulated below in Table. 1.

TABLE 1

| Ingredient | Molecular Formula | Percentage |
|---|---|---|
| Di-sodium Hydrogen Phosphate | $Na_2HPO_4$ | 2 |
| Bismuth Oxide (Bismite) | $Bi_2O_3$ | 17 |
| Tri-calcium Silicate (Hatrurite) | $Ca_3SiO_5$ | 50 |
| Di-calcium Silicate (Larnite) | $Ca_2SiO_4$ | 15 |
| Calcium Sulfate (Anhydrite) | $CaSo_4$ | 2 |
| Gypsum | $CaSO_4 \cdot 2H_2O$ | 5 |
| Strontium Carbonate | $SrCo_3$ | 3 |
| Zeolite | $M_2/nO \cdot A_{12}O_3 \cdot xSiO_2 \cdot yH_2O$ | 2 |
| Tri-calcium Aluminate | $Ca_3Al_2O_6$ | 4 |

Figure 1:
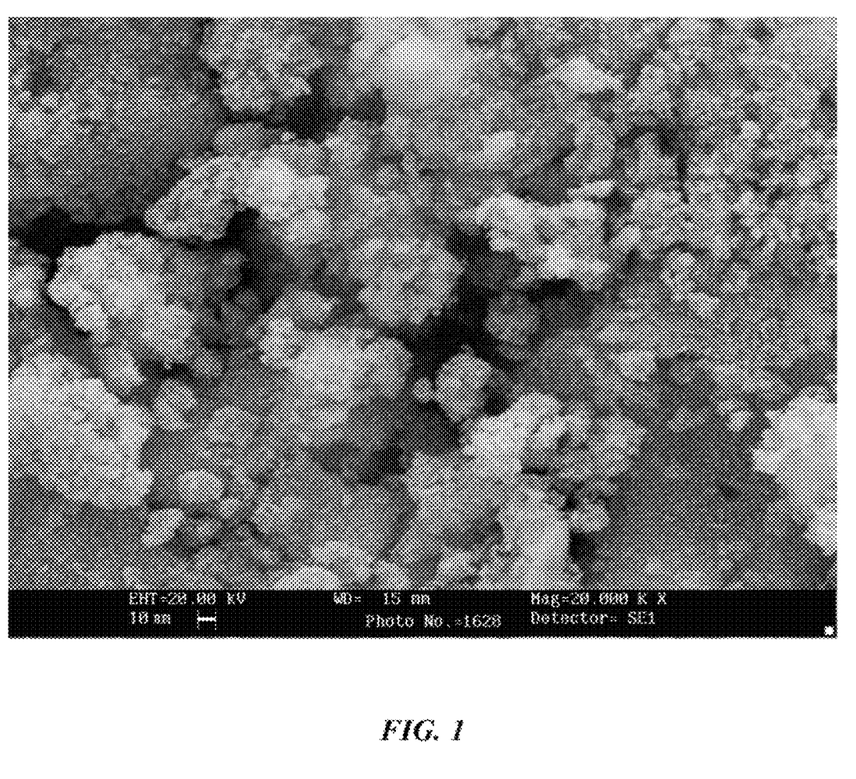
FIG. 1 is an image of a sample of the dental cement generated from a scanning electron microscope.

In order to prepare the dental cement, the ingredients thereof are mixed together in any order and are stored at predetermined temperature, pressure, and humidity (37° C., low humidity environment) for a predetermined period of time. The length of the nanoparticles of the thus prepared dental cement, which is shown in FIG. 1, range between 40 to 100 nm. In one embodiment, the composition of the dental cement of the present invention comprises distilled water or any proteinaceous buffer, such as, albumen or phosphate buffer.

Turning now to the ingredients, in one embodiment, the ingredients, di-calcium and tri-calcium silicate are prepared from sol-gel technique. Di-calcium and tri-calcium silicate are stored in vacuum at predetermined temperature, pressure, and humidity levels before being mixed with the other ingredients.

Figure 2:
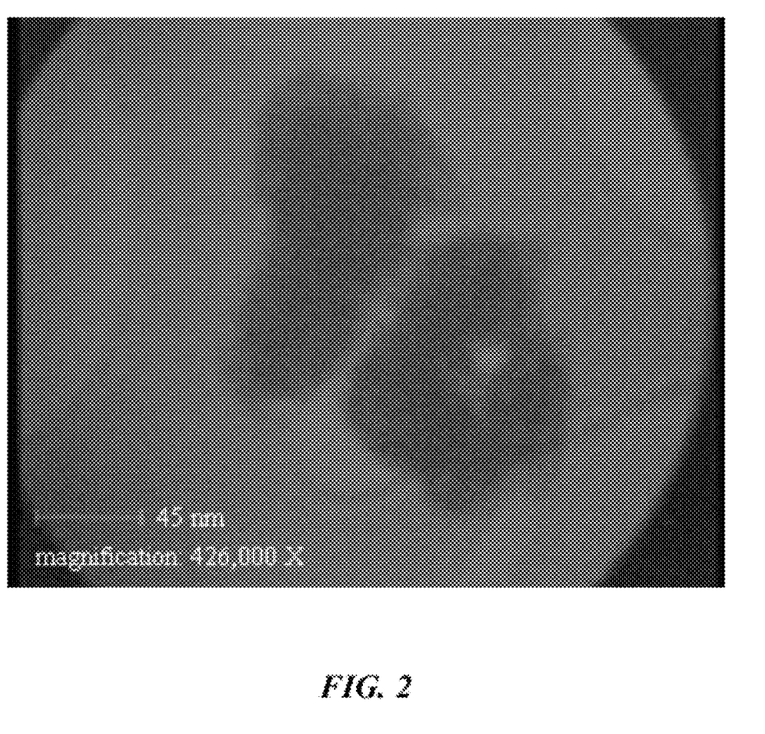
FIG. 2 is an image of rod-shaped nanoparticles of tri-calcium silicate generated from a transmission electron microscope.
Figure 3:
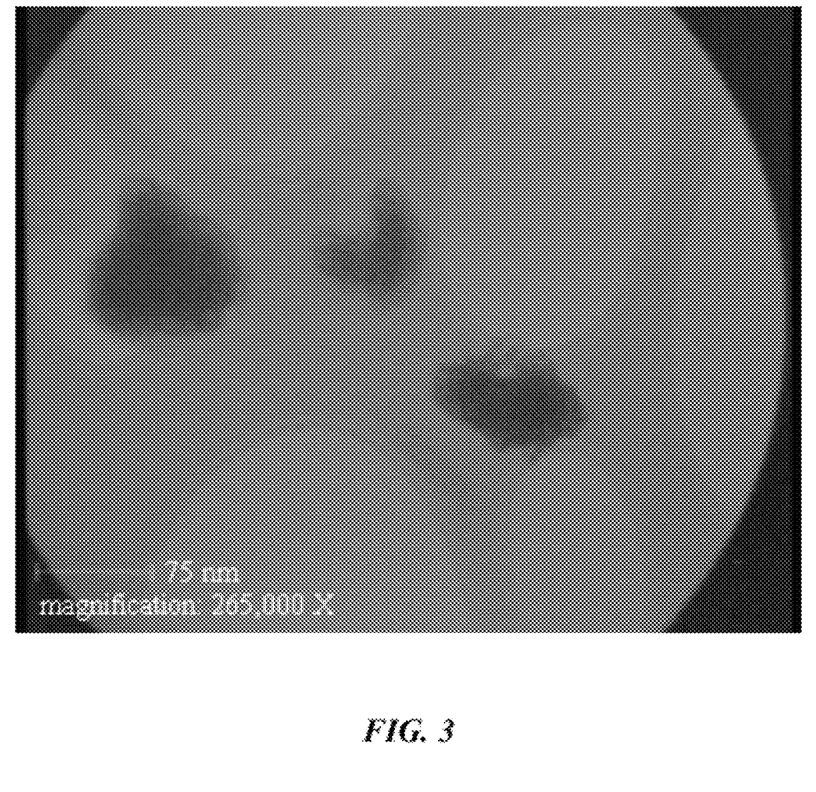
FIG. 3 is an image of globular-shaped nanoparticles of tri-calcium silicate generated from a transmission electron microscope.
Figure 4:
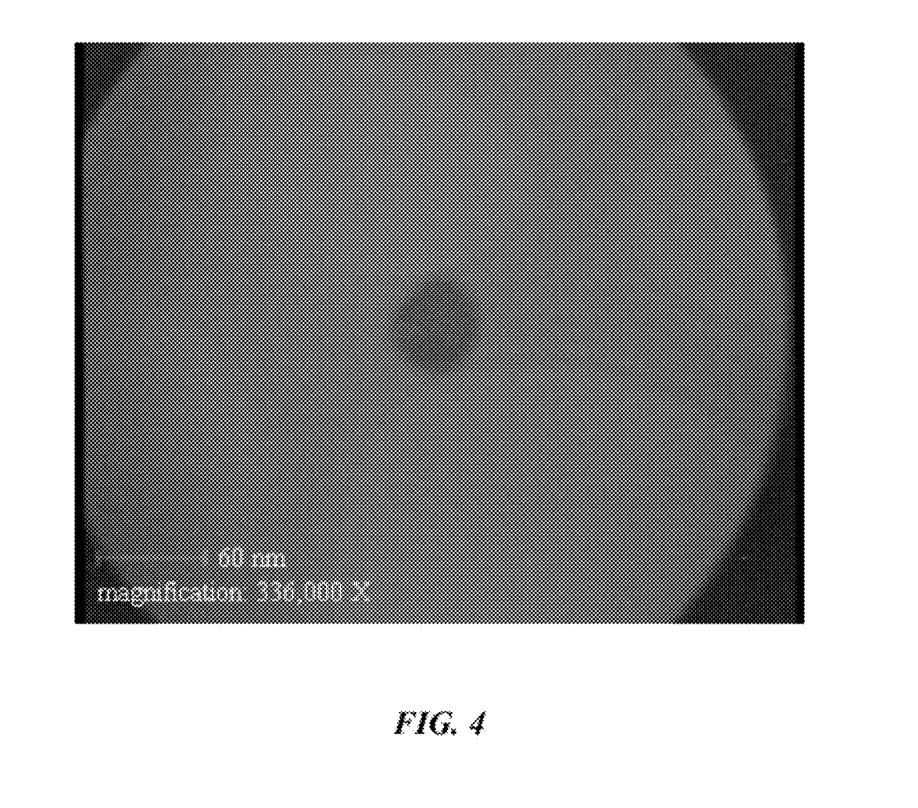
FIG. 4 is an image of spherical-shaped nanoparticles of tri-calcium silicate generated from a transmission electron microscope.

Referring to FIG. 2, in one embodiment, the nanoparticles of tri-calcium silicate have a conglomerated or rod shapes. In another embodiment, the shape of the nanoparticles of tri-calcium silicate is globular as seen in FIG. 3. In yet another embodiment, as shown in FIG. 4, the nanoparticles of tri-calcium silicate are of spherical shape. The f of the nanoparticles of tri-calcium silicate in all the three embodiments range between 40 and 60 nanometers.

The purpose for the inclusion of Zeolite is to increase the resistance of the composition material against acidic environments resulting from inflamed dental tissues. The inclusion of Zeolite also minimizes the alkali-aggregate expansion that is typically caused due to thermal treatment.

The ingredient strontium carbonate improves osteopromotive properties, and bio-activeness of the dental cement of the present invention while preventing agglomeration or clustering of the nanoparticles of the ingredients. This prevention of agglomeration ensures uniform distribution of the ingredients as can be seen in FIG. 1.

The dental cement of the present invention, compared to popular dental cements, such as, White Mineral Trioxide Aggregate (WMTA), Portland cement, and etc, exhibits, at least, a higher resistance to acidic ambience, a higher durability to ambient changes, a better hydration ability, a better inertness towards toxic ambience, a better stability with regard to organic and inorganic contaminants, a better strength, a lesser expansion, a lower porosity, an improved interfacial microstructure, induction of hydroxyapatite formulation, a better biocompatibility, a quicker setting time, especially in aqueous ambience, a quicker stimulation of hard tissue healing, a superior microhardness owing to the presence of nanoparticles, a smoother surface that enables better adhesion to the tooth structure and less gaps there between, an improved cementogenesis, and a higher osteo conductivity.

The following Table. 2 compares a few characteristics of the popular dental cements, WMTA and Portland cement, against the dental cement of the present invention:

TABLE 2

| | WMTA | Portland Cement | Dental Cement of the Present Invention |
|---|---|---|---|
| Water-to-cement powder ratio needed | 1:3 | 1:3 | 1:2 to 1:3 |
| Setting time (min) | 39.1 | 139.1 | 6.2 |
| Microhardness @7.4 pH | 52.21 | 29.32 | 85.21 |
| Microhardness @4.4 pH | 13.98 | 13.14 | 72.21 |
| Leakage (ng/mL) | 0.282 ± 0.079 | 0.410 ± 0.093 | 0.012 ± 0.011 |

Figure 5:
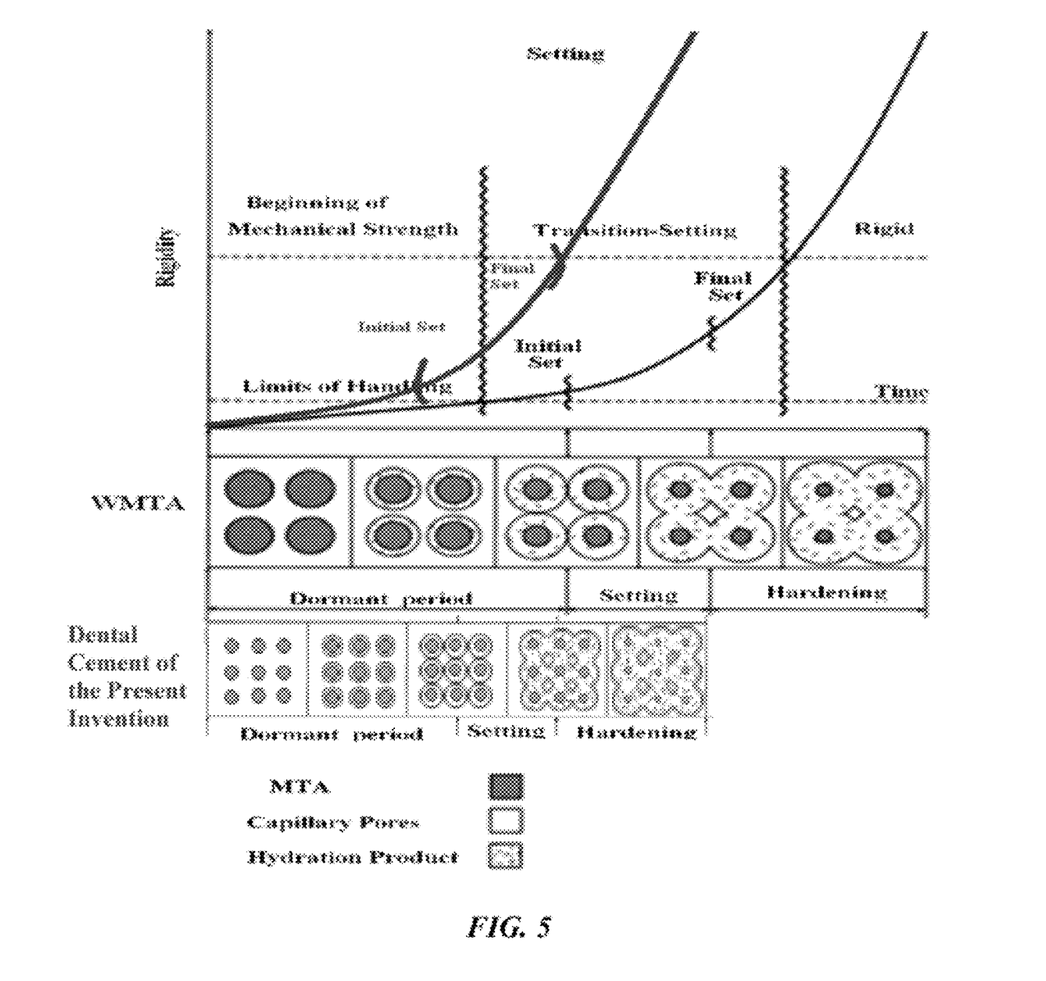
FIG. 5 is a graphical representation of the behavior of WMTA and the dental cement of the present invention against time.

Although the difference between water-to-cement powder ratio needed for the dental cement of the present invention and the other two cements is not substantial, the dental cement of the present invention exhibits a superior setting time and microhardness at the two different pH environments (4.4 pH & 7.4 pH), lesser leakage, and a lesser variation of microhardness between the two pH environments. A Gilmore apparatus is used for determining the setting time and a Vicker's microhardness tester apparatus is used for determining the microhardness. FIG. 5 depicts a graphical representation of the behavior of WMTA and the dental cement of the present invention against time. From the sectional images (below the graph) of the dental cements' samples, it can be inferred that the cement with finer particles react relatively faster. Having superior microhardness and lesser microhardness-variation prevents the dental cement of the present invention from being washed out or dislodged when exposed to a tissue which has an acidic pH. The reason for the dental cement of the present invention being better than the other two cements is due to the fact that the substance of the dental cement is relatively finer as it is composed of nanoparticles.

The dental cement of the present invention can also be used for root-end filling procedure due to its superior setting time (as depicted in Table. 2), especially in the presence of liquids—moisture and blood. More particularly, the initial and final setting times of the dental cement of the present invention is around 6 minutes and about 40 minutes respectively. It is also noteworthy that the dental cement of the present invention hardens at body temperature. In addition, by raising the pH value during the setting process, the material provides antimicrobial effect. This characteristic is particularly important when the dental cement of the present invention is in direct contact with the damaged pulp or periapical tissues.

Also, owing to the bio-activeness of the dental cement of the present invention, the same permits bio-stimulation before, during, and after the hardening process to create a water-based, calcium and phosphate-containing composition that facilitates repair and the growth of damaged tissues. This property—bio activeness—plays an important role in other endodontic procedures such as, pulpotomy, pulp capping, dental perforation repair surgery, gel injection, and dental implantation surgery and hence, the dental cement of the present invention can be used for the same procedures as well.

Studies show that size and surface area of the particles of the dental cement play an important role in physical and chemical properties thereof. More particularly, the particles with greater surface area exhibit faster reactivity and have lower porosity, which is inversely proportional to microhardness.

The dimensional characteristics of the dental cement of the present invention related to the specific surface area are depicted in the following Table. 3, wherein the characteristics are determined using Brunauer, Emmett, and Teller (BET) theory.

TABLE 3

| | |
|---|---|
| Surface Area | 7.8843 Sq. m/g |
| Slope | 2.143075 |
| Y-intercept | 0.075989 |
| C | 29.202578 |
| VM | 0.0450641 |
| Correlation Coefficient | 9.9951e−001 |

Figure 6:
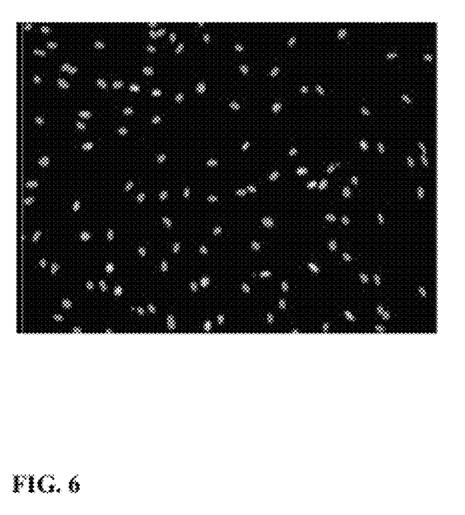
FIG. 6 shows EDS dot map of WMTA and the dental cement of the present invention.

Referring to FIG. 6, an EDS color dot map was used to evaluate the elemental distribution of materials for WMTA and the dental cement of the present invention. The EDS analysis was performed twice for each gold-coated sample of each of the cement samples at ×1000 magnification. Low magnification was selected to observe the type of elemental distribution over the texture. The difference between the constituent elements of the dental cement of the present invention and WMTA was related to the presence of strontium with a uniform distribution on texture. The high magnification (×5000) was selected to view porosity and crystal formations within a sample only for SE mode of SEM. In the case of the dental cement of the present invention, a constant and uniform nonporous gray image was observed, which might be ascribed to a more proper hydration of products and good interlocking of the solid than WMTA. However, initial setting time of the dental cement of the present invention is about 6 minutes. Despite the lack of significant differences in chemical composition of WMTA and the dental cement of the present invention, the difference in initial setting time might be attributed to the total surface area of dental cement of the present invention and some trace material that prevents the agglomeration of cement particles together. This would mean that the dental cement of the present invention may react faster with water, leading to quicker setting properties.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

Although the embodiments herein are described with various specific embodiments, it will be obvious for a person skilled in the art to practice the invention with modifications. However, all such modifications are deemed to be within the scope of the claims.

It is also to be understood that the following claims are intended to cover all of the generic and specific features of the embodiments described herein and all the statements of the scope of the embodiments which as a matter of language might be said to fall there between.

What is claimed is:

1. A dental cement composition made up of ingredients comprising the nanoparticles of Di-calcium Silicate ($Ca_2SiO_4$), Tri-calcium Silicate($Ca_3SiO_5$), Bismuth Oxide ($Bi_2O_3$), Gypsum, Strontium Carbonate($SrCo_3$), Zeolite, Calcium Sulfate ($CaSo_4$), Di-sodium Hydrogen Phosphate ($Na_2HPO_4$), Tri-calcium Aluminate ($Ca_3Al_2O_6$).

2. The composition of claim 1 wherein said composition is prepared by mixing the ingredients under vacuum at a predefined pressure.

3. The composition of claim 1, wherein the length of the nanoparticles of the composition range between 40 nm and 100 nm.

4. The composition of claim 1, wherein the nanoparticles of tricalcium silicate are rod shaped.

5. The composition of claim 1, wherein the nanoparticles of tricalcium silicate are globular shaped.

6. The composition of claim 1, wherein the nanoparticles of tricalcium silicate are spherical shaped.

7. The composition of claim 1, wherein dicalcium silicate and tricalcium silicate are prepared from sol-gel technique.

8. The composition of claim 1 mixed with distilled water before usage.

9. The composition of claim 1 mixed with proteinaceous buffer before usage.

10. The composition of claim 9, wherein the proteinaceous buffer comprises albumen.

11. A dental cement composition comprising the nanoparticles of dicalcium and tricalcium silicate, bismuth oxide, gypsum and strontium carbonate, Zeolite, wherein, dicalcium silicate, tricalcium silicate, bismuth oxide, gypsum, strontium carbonate, and Zeolite make up 15, 50, 17, 5, 3, and 10 percentage of the composition of the dental cement.

* * * * *